United States Patent [19]

Rubenstein et al.

[11] 4,423,143

[45] * Dec. 27, 1983

[54] β-D-GALACTOSIDASE CONJUGATE FOR ENZYME IMMUNOASSAYS

[75] Inventors: Kenneth E. Rubenstein, Menlo Park; Edwin F. Ullman, Atherton, both of Calif.

[73] Assignee: Syva Company, Palo Alto, Calif.

[*] Notice: The portion of the term of this patent subsequent to Jun. 18, 1991, has been disclaimed.

[21] Appl. No.: 258,848

[22] Filed: Apr. 29, 1981

Related U.S. Application Data

[60] Continuation-in-part of Ser. No. 221,235, Dec. 30, 1980, Pat. No. 4,376,825, which is a division of Ser. No. 36,929, May 7, 1979, Pat. No. 4,282,325, which is a continuation-in-part of Ser. No. 857,145, Dec. 5, 1977, Pat. No. 4,203,802, which is a division of Ser. No. 722,964, Sep. 13, 1976, Pat. No. 4,067,774, which is a continuation of Ser. No. 481,022, Jun. 20, 1974, abandoned, which is a division of Ser. No. 304,157, Nov. 6, 1972, Pat. No. 3,852,157, which is a continuation-in-part of Ser. No. 802,683, Jun. 2, 1977, Pat. No. 4,190,496, which is a continuation of Ser. No. 760,499, Jan. 19, 1977, Pat. No. 4,191,613, which is a continuation-in-part of Ser. No. 722,964, Sep. 13, 1976, Pat. No. 4,067,774.

[51] Int. Cl.$^3$ .................. G01N 33/54; C12N 9/96
[52] U.S. Cl. ............................. 435/7; 435/188
[58] Field of Search .................... 435/188, 7

[56] References Cited

U.S. PATENT DOCUMENTS

| 3,905,871 | 9/1975 | Rubenstein et al. | 435/7 |
| 3,975,237 | 8/1976 | Rubenstein et al. | 435/7 |
| 4,067,774 | 1/1978 | Rubenstein et al. | 435/7 |
| 4,190,496 | 2/1980 | Rubenstein et al. | 435/7 |

Primary Examiner—Alvin E. Tanenholtz
Attorney, Agent, or Firm—Bertram I. Rowland

[57] ABSTRACT

β-D-Galactosidase conjugates for use in homogeneous immunoassays. β-D-Galactosidase is conjugated with analytes and the resulting conjugates are combined with receptors for the analyte and a sample suspected of containing the analyte. The resulting enzymatic activity is compared to standard assay media for quantitative determination of the analyte.

5 Claims, No Drawings

β-D-GALACTOSIDASE CONJUGATE FOR ENZYME IMMUNOASSAYS

CROSS-REFERENCE TO RELATED APPLICATIONS

This application is a continuation-in-part of application Ser. No. 221,235 filed Dec. 30, 1980, now U.S. Pat. No. 4,376,825, which is a divisional of application Ser. No. 036,929, filed May 7, 1979, now U.S. Pat. No. 4,282,325, which is a continuation-in-part of application Ser. No. 857,145, filed Dec. 5, 1977, now U.S. Pat. No. 4,203,802 which application is a divisional of application Ser. No. 722,964, filed Sept. 13, 1976, now U.S. Pat. No. 4,067,774, which was a continuation of application Ser. No. 481,022, filed June 20, 1974, now abandoned, which was a divisional of application Ser. No. 304,157, filed Nov. 6, 1972, now U.S. Pat. No. 3,852,157, which was a continuation-in-part of application Ser. No. 802,683, filed June 2, 1977, now U.S. Pat. No. 4,190,496, which is a continuation of application Ser. No. 760,499, filed Jan. 19, 1977, now U.S. Pat. No. 4,191,613, which was a continuation-in-part of application Ser. No. 722,964, which file history is set forth above.

BACKGROUND OF THE INVENTION

1. Field of the Invention

Immunoassays have shown themselves to be extremely versatile in allowing for methods to determine the presence of a particular substance, even when a wide variety of other materials of similar or different structure are present in the unknown sample. The immunoassays rely on the ability of an antibody to specifically detect or bind to an haptenic or antigenic organic compound, while not interacting with other compounds. The divalent nature of the antibody and/or its high molecular weight, 150,000 or greater, allow for a discrimination between a compound which is bound and a compound which is not bound to antibody. Among various immunoassays involving antibodies are radioimmunoassays, spin immunoassay, homogeneous enzyme immunoassay, available under the trademark EMIT, supplied by Syva Company, and hemeagglutination.

The enzyme immunoassay is extremely versatile in permitting spectrophotometric determinations. The immunoassay employs an enzyme to which an organic compound—a ligand—is conjugated at a position where when bound to receptio, the activity of the enzyme is substantially reduced. To the extent that the unknown sample contains the same ligand the amount of receptor available for binding to the organic compound conjugated to the enzyme is reduced. Therefore, by analyzing for enzymatic activity, a significant increase in enzymatic activity over the enzymatic activity in the absence of the unknown indicates the presence of the ligand in the unknown.

The sensitivity of the homogeneous enzyme immunoassay is based to a substantial degree on the activity of the enzyme when conjugated and the degree of inhibitability when receptor is bound to the ligand conjugated to the enzyme. It is, therefore, desirable to have an enzyme which not only has a high turnover rate initially, but retains a substantial proportion of this turnover rate after conjugation, and is strongly inhibited when receptor is bound to the ligand which is conjugated to the enzyme. Also, the enzyme should allow for strong specific binding of receptor to the conjugated ligand.

2. Description of the Prior Art

An homogeneous enzyme immunoassay system has been sold under the trademark EMIT employing haptens conjugated to lysozyme, where the enzymatic activity is determined by the reduction in turbidity as a result of lysis of bacterial walls. Numerous publications concerning the system have issued since May 7, 1971, see for example, Rubenstein, et al., Biochem. & Biophysical Res. Comm. 47, 846 (1972). U.S. Pat. No. 3,654,090 teaches a heterogeneous immunoassay employing such enzymes as peroxidase, amyloglucosidase, and β-D-galactosidase with antigens.

SUMMARY OF THE INVENTION

Ligand conjugates to β-galactosidase are provided for employment in homogeneous enzyme immunoassays to provide high sensitivity in detecting extremely small amounts of organic materials. Ligand is conjugated by relatively short chains or linking groups to β-galactosidase to provide a product which can be used in a homogeneous enzyme immunoassay. With most ligands, the resulting conjugate retains a substantial proportion of the original enzyme activity and has a high degree of inhibitability with an antiligand receptor, usually in excess of 50% of the activity of the conjugated β-galactosidase. The linking chains conveniently employ a non-oxo-carbonyl group or a single covalent bond to saturated carbon.

DESCRIPTION OF THE SPECIFIC EMBODIMENTS

β-Galactosidase conjugates to ligands are provided finding use in enzyme immunoassays. The ligands may be haptenic or antigenic. Depending upon the size of the ligand, there may be one or more ligands per β-galactosidase or one or more β-galactosidases per ligand.

The β-galactosidase-bound-ligand will usually have molecules of ligand to enzyme subunit ratios on the average over the entire composition in the range of 0.02–40:1 frequently 0.05–15:1, and more frequently about 0.1–5:1, wherein the number of ligands when the ligand is a protein is expressed as the number of ligand molecules times the number of its component polypeptide chains. For small ligands (less than about 10,000 molecular weight, generally from about 100 to 2,000 molecular weight, usually from about 125 to 1,000 molecular weight), there will usually be at least one ligand, more usually at least two ligands per enzyme, while with large ligands (greater than about 5,000 molecular weight), there will generally be at least one enzyme per ligand. In the area of overlap, the ratio will depend on the nature of the ligand, among other factors to be discussed.

The number of small ligands per β-galactosidase will be affected to some degree by the molecular weight of the particular β-galactosidase. Normally, the fewer molecules of ligand bound to an enzyme to achieve the desired degree of inhibitability per receptor, the more sensitive the assay. Usually, the range of small ligands will be from 1 to 24, more usually 2 to 20, with random substitution.

With large ligands there will be on the average not more than one β-galactosidase per 4,000 molecular weight, more usually not more than one β-galactosidase per 6,000 molecular weight.

For convenience, the β-galactosidase compositions may be characterized by the following formula:

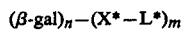
$(β\text{-gal})_n—(X^*—L^*)_m$ wherein:

β-gal intends β-galactosidase subunit;
X* is a bond or linking group;
L* is a ligand;
n and m are each at least one and n is not greater than the molecular weight of L* divided by 6,000 and m is not greater than 24.

The linking group will vary widely, depending upon the nature of the ligand. Where the linking group X* is other than a bond, X* will normally have at least one of the following functionalities: Mercapto, activated ethylene, usually carbonyl activated, non-oxo carbonyl (including the nitrogen-imino- and thio-thiocarbonyl-analogs thereof), and diazo, including combinations thereof.

Exemplary linking groups are α-carboxymethine, carbamoylmethylene (—NHCOCH$_2$—), iminoxyacetyl (═NOCH$_2$CO—) p-oxybenzoyl, maledioyl, succindioyl, ethyleneoxyacetyl, N-methyl 3-aza-1-iminopentylene (—(CH═C)—CH$_2$N(CH$_3$)CH$_2$CH$_2$CH$_2$—), and m-(N-maleimido)benzoyl, and the like.

For the most part, poly(amino acid) conjugates with β-galactosidase will have the following formula:

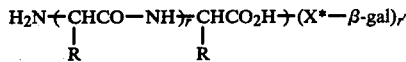
$H_2N\text{---}(CHCO\text{---}NH)_{r}\text{---}(CHCO_2H)\text{---}(X^*—β\text{-gal})_{r'}$
$\qquad\;\; R \qquad\qquad\;\; R$ wherein:

X* has been defined previously;
β-gal has been defined previously;
R is the side chain of an amino acid residue or hydrogen;
r is an integer from 1 to 1,000, more usually from 1 to 500, and most commonly from 2 to 100;
r' is an integer of at least 1 and not greater than the molecular weight of the poly(amino acid) divided by 2,000.

Polypeptides of interest are ACTH, oxytocin, luteinizing hormone, insulin, Bence-Jones protein, chorionic gonadotropin, pituitary gonadotropin, growth hormone, rennin, thyroxine binding globulin, bradykinin, angiotensin, follicle stimulating hormone, immunoglobulens A, D, E, G and M, α-lipoproteins, nucleoproteins, and miscellaneous proteins, etc.

The next group of compounds are the steroids, which include the estrogens, gestogens, androgens, adrenocortical hormones (glucocorticoids and mineral corticoids), bile acids, and cardiotonic glycosides or aglycones.

For the most part, the steroids used have the following formula:

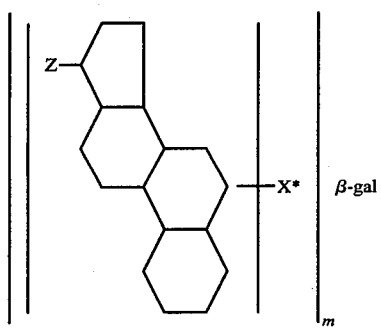

where:

X*, β-gal and m have been defined previously;
Z is hydrogen or a functionality or side chain associated with a particular class of steroids. Any one of the ring positions, usually the 2,3,4,6,10,11,16 or 17 positions or a side chain of Z may be substituted with X*, and when substituted to X*, can have the normal functionality associated with the particular steroid.

The cardiotonic glycosides and aglycones will for the most part have the following formula:

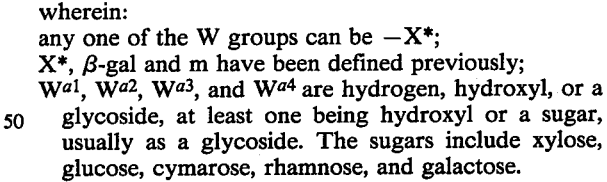

wherein:

any one of the W groups can be —X*;
X*, β-gal and m have been defined previously;
W$^{a1}$, W$^{a2}$, W$^{a3}$, and W$^{a4}$ are hydrogen, hydroxyl, or a glycoside, at least one being hydroxyl or a sugar, usually as a glycoside. The sugars include xylose, glucose, cymarose, rhamnose, and galactose.

Numerous other compounds may be conjugated to β-galactosidase employing the same types of sites for linking to the ligand and the same types of linking groups as exemplified above.

In preparing the conjugates, it is desirable that at least 2%, preferably at least 10% and particularly preferred at least 40% of the original enzyme activity is retained. Furthermore, the enzyme is substituted in such a manner so that when one or more ligands are bonded to the enzyme, the activity of the enzyme is reduced by at least 30% of its original activity after conjugation, usually at least 40% and preferably by at least 50% when bound by a receptor, e.g. antibody.

It will usually be necessary to employ macromolecular substrates. Of particular interest is a polysaccharide macromolecular support to which is attached a galactosidyl ether of nitrophenol or umbelliferone. See particularly U.S. patent application Ser. No. 28,777, filed Apr. 10, 1979, now U.S. Pat. No. 4,268,663. Another macromolecular substrate is described in Madhave et al., Enzyme 25, 127-131 (1980). Various other β-galactoside derivatives may serve as substrates for the enzyme. The enzyme is a well characterized one and there are ample examples of substrates in the literature.

Various ways can be employed for conjugating the various ligands to the β-galactosidase. The conditions employed will normally reflect the particular functionality which is employed in forming a bond to the β-galactosidase. Where the ligand is a poly(amino acid) it is convenient in the absence of naturally present mercapto groups to modify the ligand that will react with mercapto groups, normally on the enzyme. Illustrative of such groups are maleimido and N-bromoacetyl. One linking group that can be used is the commercially available maleimidobenzoyl ester, particularly the N-hydroxy succinimide ester. With haptenic ligands, the ligand may be modified to introduce a carbonyl group, particularly a non-oxo-carbonyl group, which may then be used as an active ester to form amide bonds with the enzyme.

For coupling to the enzyme, the reaction mixture will normally be brought to a pH in the range of about 5 to 10, more usually in the range of about 6 to 9. Various buffers may be used, such as phosphate, carbonate, tris, and the like. An aqueous solvent will normally be used, and up to about 40 weight percent of an oxyethylene alcohol or ether having from 1 to 3 oxyethylene units may be present. Particularly useful is carbitol. The temperatures will normally be at or above $-5°$ C. and generally less than about 40° C., usually from about 0° to 25° C.

The concentration of the enzyme in the coupling reaction mixture will vary widely, generally ranging from about 0.05 to 5, more usually from about 0.1 to 1 mg/ml. The amount of ligand to be conjugated will vary, depending upon the nature of the ligand and the ligand-enzyme ratio which is desired.

EXPERIMENTAL

The following examples are offered by way of illustration and not by way of limitation.

All temperatures not otherwise indicated are in centigrade. All percents not otherwise indicated are by weight, except for mixtures of liquids, which are by volume.

EXAMPLE A

Purification of β-galactosidase for conjugation

Into 2.5 ml of chromatographic buffer (PBS+5 mM $NaN_3$+0.1 mM $Mg(OAc)_2$) was dissolved a pellet obtained from 3 ml of a suspension of β-galactosidase in 2.2 M ammonium sulfate (pH 6, 11.3 mg/ml, Boehringer Mannheim Biochemicals), the solution clarified by centrifugation and then chromatographed on a 56×2.5 cm column containing Biogel A5M. A flow rate of 11.7 ml/hr was maintained taking 3.89 ml fractions. Tubes 51-58 inclusive were pooled which with washings provided a total volume of 32.65 ml, having a concentration of 0.7 mg/ml, based on absorption at 280 nm.

EXAMPLE I

Human Albumin Conjugate To β-galactosidase

In a reaction vessel was combined 10.5 ml of a 10 mg/ml human albumin solution in 50 mM Pi(Na$^\oplus$), pH 7.0 and 0.2 ml of a 12.5 mg/ml solution of N-ethyl maleimide (NEM) in DMF, and the mixture incubated overnight at room temperature (rt). The reaction mixture was then dialysed 3×500 ml against 50 mM Pi(Na$^+$), pH 7.0 at rt overnight. Before using, the residue was further dialysed 2×500 ml 50 mM Pi(Na$^\oplus$), pH 7, degassed.

β-galactosidase (Example A) was dissolved in 6 ml of dialysis buffer to a concentration of 1.02 mg/ml and dialyzed 2×500 ml 50 mM Pi(Na$^\oplus$), pH 7.0, 1 mM $Mg(OAc)_2$, at rt overnight.

Into a reaction vessel was combined 4 ml of a 9.8 mg/ml solution of the NEM capped human albumin and 50 μl of a 50 mg/ml solution of m-maleimidobenzoic acid N-hydroxy succinimide ester (MBSE) in dry DMF and the reaction allowed to proceed for 30 min at rt. To the mixture was then added 0.8 ml of 1 M HOAc(Na$^\oplus$), pH 5.0.

The reaction mixture was then chromatographed on Sephadex G25M (22×2.5 cm), eluting with 20 mM HOAc(Na$^\oplus$), pH 5.0, 0.15 M NaCl, collecting 100 drop fractions Tubes 5 and 6 were pooled.

The conjugation of β-galactosidase with human albumin was performed in triplicate.

EXAMPLE II

Human IgG conjugate to β-galactosidase

To a solution of 6.17 ml of HIgG (14c labeled), (5 mg/ml) in 50 mM Pi (Na$^+$) pH 7.0, was added with rapid stirring 0.2 ml of MBSE (10 mg/ml in dry DMF) and the reaction allowed to proceed for 0.5 hr at 22° C. under $N_2$. To the mixture was then added 1 ml 1 M NaOAc, pH 5.0 and the mixture chromatographed on Sephadex G25F, eluted with 20 mM NaOAc, pH 5.0, 0.15 M NaCl and 100 drop fractions taken, with fractions 5-7 pooled. Assaying for MBSE with cysteine and 5,5'-dithiobis-(2-nitrobenzoic acid) showed ~7 Maleinide groups per molecule.

To 11.85 ml of a solution of the functionalized HIgG (20 mg) in the above acetate buffer, was added 2 ml (1.36 mg) of a solution of β-galactosidase in 50 mM Pi, pH 7.0, 0.1 mM $Mg(OAc)_2$, 1.25 ml 0.5 M Pi (Na$^\oplus$), pH 7.0 and the reaction allowed to proceed under $N_2$ at room temperature for 21 hrs. Any unreacted maleimidyl groups were capped by adding 0.090 ml of 10 mM cysteine HCl and incubating at room temperature for 0.5 hr. The derivative was concentrated under $N_2$ by ultrafiltration (Amicon PM10 membrane) to a final volume of ~2 ml.

The conjugate was then chromatographed on a 82×1.5 cm Biogel A5M column with PBS/5 mM $NaN_3$/1 mM $Mg(OAc)_2$ eluent at a rate of 4.8 ml/hr collecting 2.53 ml fractions. Fractions 25-34 were pooled. The enzyme was assayed with o-nitrophenyl β-galactoside, 0.1 ml (20 mM) diluted in 0.4 ml buffer, 0.1 M Pi(Na$^\oplus$), pH 7.6, 2 mM $MgCl_2$, 1 mg/ml RSA, added to 0.01 ml of the conjugate diluted with 0.5 ml buffer and the change in absorption at 420 nm, 37° C., from 10 to 40 sec after mixing determined. Based on the radioactivity of tagged HIgG and the enzyme activity, a ratio of 7.5 moles of HIgG per mole β-galactosidase was found.

EXAMPLE III

Digoxin Conjugate to β-galactosidase

To 50 μl of DMF was added 10 milligrams of the carboxymethyloxime of digoxigenin, 2.9 milligrams of N-hydroxy succinimide, 4.8 mg of 1-ethyl-3-(3-dimethylaminopropyl)carbodiimide HCl, and the mixture stirred for 15 min at 20° C. A pellet obtained by centrifugation of a solution of 0.3 ml (5 mg) of an ammonium sulfate suspension of β-galactosidase was dissolved in 100 μl of 0.05 M Pi(Na⊕), 0.15 M NaCl, 0.001 M MgCl$_2$ pH 7 and the activated ester prepared above was added in 1 μl aliquots with stirring at 5 min intervals and the enzyme activity monitored after each addition. A total of 7 μl was added. The reaction was quenched by a 1:50 dilution of the conjugate in 0.5 M tris, 0.16 M citrate, 1.5 M NaCl, 0.01 M MgCl$_2$, 0.5% w/v NaN$_3$, pH 7.0. The product was dialyzed at 4° C. 4×2 L of a 1:10 dilution of the above buffer followed by the addition of 1% w/v rabbit serum albumin to the residue. An assay of the enzyme conjugate according to the protocol, infra, showed that $10^{-9}$ M of digoxin in an assay mixture could be detected.

EXAMPLE IV

Preparation of a conjugate of o-nitrophenyl β-galactoside and dextran with di(3-aminopropyl)piperazine spacer A. To 7 ml of 1.8 N Na chloroacetate solution and 3 ml water was added 2 g dextran T2000 (Pharmacia), followed by the addition of 10 ml 2.5 N aq.NaOH, and the mixture heated at 70°–75° for 1.5 hr and allowed to stand overnight. To the mixture was added 2 ml glac. HOAc and the mixture then dialyzed against 10 L 5% aq. HOAc (4×24 hr) and then against deionized H$_2$O, 10 L (4×24 hrs). By employing radioactively labeled chloroacetate, it was found that there were about 1.21 μmoles of carboxymethyl per mg of dextran.

B. To 80 ml of an aqueous solution containing 1.96 mmole of the carboxymethyldextran prepared above was added 8 ml (40 mmole) of N,N'-bis-(3-aminopropyl)piperazine and the solution adjusted to pH 4.75 with HCl, followed by adding 18 g (90 mmole) EDCI and allowing the solution to stand at rt for 24 hrs. The reaction mixture was then dialized against 12 L deionized water containing 150 g K$_2$HPO$_4$ and 75 g KH$_2$PO$_4$ (4×25 hrs) and the number of amino groups determined by employing trinitrobenzenesulfonic acid was found to be 68% of the available carboxy groups.

C. To 10 ml DMF was added 387 mg 2-nitro-5-carboxyphenyl-β-galactoside, 249 mg EDCI and 151 mg N-hydroxy succinimide and the mixture stirred at rt for 1 hr. To 10 ml of aqueous solution containing the aminosubstituted dextran prepared above (9.2 mM in amino groups) was added 2.5 ml of the NHS ester prepared above and the reaction mixture stored at rt for 24 hrs. The reaction mixture was dialyzed against water (4×) and the product assayed for o-nitrophenyl-β-galactoside groups (ONPG). The product was found to be 7.0 mM/ml in ONPG groups by UV.

EXAMPLE V

Conjugation of HIgG and β-galactosidase

A reaction mixture was prepared by combining 4 ml HIgG (8.34 mg/ml, 50 mM phosphate buffer, pH 7.0), 2.17 ml phosphate buffer, pH 7.0, and 20 μl of a DMF solution of m-(N-maleimidyl)benzoic acid N-hydroxy succinimide ester (10 mg/ml) added with rapid stirring. After 30 min under N$_2$ at room temperature to the reaction was added 1 ml 1 M NaOAc to adjust the pH to 5. The mixture was then chromatographed on Sephadex G25F (2.4×20 cm), eluted with 20 mM NaOAc, pH 5.0, containing 0.15 M NaCl at a rate of 30 ml/hr, collecting 6.6 ml fractions. Fractions 5–7 were pooled. Analysis by titration with cysteine showed about 7 maleimide groups per HIgG.

The maleimide modified HIgG was diluted with phosphate buffer followed by addition to 2 ml of a β-galactosidase solution in 50 mM phosphate buffer, pH 7.0 (0.67 mg/ml), to provide a final reaction volume of 14.1 ml. The following table indicates the various amounts of solution added for three preparations.

| Conjugate | Maleimide HIgG ml | Maleimide HIgG mg | Phosphate Buffer, pH7 0.5M ml | Phosphate Buffer, pH7 0.05M ml |
|---|---|---|---|---|
| 1 | 1.5 | 2.54 | .15 | 10.45 |
| 2 | 5.0 | 8.45 | .50 | 7.60 |
| 3 | 11.85 | 20.03 | 1.25 | — |

The reaction was carried out at rt for 21 hrs under N$_2$. Any remaining maleimide groups were reacted with cysteine-HCl. The solutions were concentrated under N$_2$ with an Amicon Ultrafiltration cell over a PM30 membrane (conjugates 1 & 2), PM10 membrane (conjugate 3) to a final volume including wash of about 2 ml. The three samples were then chromatographed on Biogel A5M (82×1.5 cm) with PBS, 5 mM NaN$_3$, 1 mM Mg(OAc)$_2$, eluting at 4.8 ml/hr and collecting fractions of about 2.5 ml. With Conjugate 3 as exemplary, fractions 25 to 34 were pooled and assayed. Approximately 67% of the enzyme activity was recovered as conjugate product. Based on radioactive counting of radioactively labeled HIgG, approximately 81% of the HIgG was recovered in total. The concentration of enzyme in the pool of conjugates was 31.45 μg/ml, while the concentration of HIgG was 83.4 μg/ml.

EXAMPLE VI

Preparation of rabbit anti(HIgG) (Ranti (HIgG)) conjugated to Sepharose 4B Beads Into a reaction vessel was introduced 2 ml containing 7.5 mg of rabbit anti(HIgG) in 0.1 M NaHCO$_3$, pH 8.1, 0.5 M NaCl and 0.9 ml CNBr activated Sepharose 4B beads and the mixture stirred at 4° for 6 hrs, followed by stirring at rt for 2 hrs. To the mixture was then added 0.1 volume 1 M 2-aminopropanol, pH 8.0, and the mixture stirred overnight at 4°. By employing radioactive Ranti(HIgG), it was found that 6.6 mg had coupled.

The beads (protein ~5 mg/ml packed beads) were washed by sequential suspension in 1×PBS (0.5 hr), and centrifugation (3×). After suspending the beads in twice their volume of PBS, 1.5 ml of the suspension was exposed to the small probe of a Sonicator (model W185 System, Ultrasonics Inc.) at power 60 watts (setting ~1.5). The sample was cooled in an ice-bath and sonicated for 3 min, followed by centrifugation, resuspension and an additional 2 min sonication as above. To demonstrate the use of the subject compositions, the following assay was carried out.

The assay employed the following reagents:

Buffer: PBS, 0.1% RSA, 5 mM NaN₃, 0.1 mM Mg(OAc)₂

Particles: (Ex. VI) RantiHIgG in buffer at 0.02 ml/ml

Conjugate HIgG-β-galactosidase: Ex. V (conjugate #1) in buffer at 9 μg β-galactosidase/ml HIgG: 5.0 mg/ml in PBS, 5 mM NaN₃, further diluted as indicated Substrate: (Ex. IV) ONPG-Dextran (2 M mol. wt.), 4 mM ONPG in PBS, 5 mM NaN₃

The protocol was as follows: combine each of 50 μl of the conjugate solution, 50 μl of HIgG solution and 50 μl of the particles with 100 μl of buffer and combine the diluted reagents in that order. Incubate at rt for 3 hrs. Add 0.1 ml substrate and 0.4 ml buffer and aspirate the mixture into a spectrophotometer cell and read the change in absorbance (420 nm) at 37° between 10 and 40 sec after adding the substrate. The following table indicates the results.

| Tube | Particles[1] | HIgG dilution[2] | Rate (min$^{-1}$) | Activity % |
|---|---|---|---|---|
| 1 | − | inf. | 0.776 | (100) |
| 2 | + | inf. | 0.186 | 24 |
| 3 | + | 16384 | 0.150 | 19 |
| 4 | + | 4096 | 0.196 | 25 |
| 5 | + | 1024 | 0.328 | 42 |
| 6 | + | 256 | 0.548 | 71 |
| 7 | + | 64 | 0.702 | 90 |
| 8 | + | 16 | 0.762 | 98 |
| 9 | + | 4 | 0.768 | 99 |
| 10 | + | 1 | 0.762 | 98 |

[1] − buffer; + particles
[2] inf. - HIgG solution substituted with buffer. HIgG solution serially diluted four-fold.

The above results demonstrate an assay for HIgG covering a concentration range of about 300 fold ranging from about 100 to 0.3 nM.

The β-galactosidase conjugates find use in homogeneous enzyme immunoassays for the determination of a wide variety of analytes, both haptenic and antigenic. The enzyme is stable, well-characterized and can be readily conjugated to analytes of interest.

Although the foregoing invention has been described in some detail by way of illustration and example for purposes of clarity of understanding, it will be obvious that certain changes and modifications may be practiced within the scope of the appended claims.

What is claimed is:

1. An enzyme conjugate of β-D-galactosidase bonded to on the average with from about 1 to 24 haptens of molecular weight of from about 125 to 1,000 and having at least one heteroatom, wherein said conjugated enzyme retains at least about 10% of the original enzyme activity and wherein the enzymatic activity of the conjugate is reduced by at least 30%, when said haptens are bound to receptors for said haptens.

2. An enzyme conjugate of β-D-galactosidase of the formula $$(\beta\text{-gal})_n-(X^*-L^*)_m$$

wherein:

β-gal intends 62 β-D-galactosidase;

X* is a bond or linking group;

L* is a ligand of from about 125 to 1,000 molecular weight and having at least one heteroatom;

n is 1; and m is in the range of 2 to 20 per subunit.

3. An enzyme conjugate of the formula:

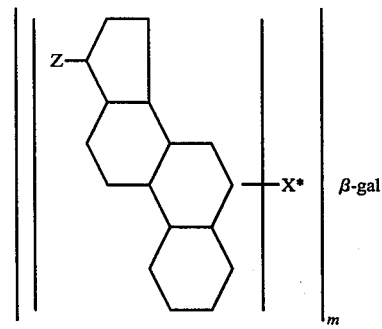

wherein:

β-gal is β-D-galactosidase;

X* is a bond or linking group;

Z is hydrogen or a functionality or side chain associated with a steroid;

any one of the ring carbons may be substituted; and m is 2 to 20 per subunit.

4. A β-D-galactosidase conjugate with digoxigenin.

5. A method for determining the presence of a ligand in a medium suspected of containing said ligand, which comprises bringing together in an aqueous liquid zone: (1) said medium; (2) soluble β-D-galactosidase-bound-ligand; and (3) soluble receptor having sites common to and capable of binding to said ligand and said enzyme-bound ligand;

wherein said receptor is at a concentration resulting in substantial reduction in enzymatic activity of said β-D-galactosidase-bound-ligand in the absence of ligand; and analyzing in said zone for the effect of said medium on the enzymatic activity of said β-D-galactosidase-bound-ligand.

* * * * *